United States Patent [19]

Rescalli et al.

[11] 3,980,528
[45] Sept. 14, 1976

[54] SOLVENT SEPARATION OF DIOLEFINS FROM MIXTURES CONTAINING THE SAME

[75] Inventors: Carlo Rescalli, San Donato Milanese; Alessandro Vetere, Milan, both of Italy

[73] Assignee: Snam Progetti S.p.A., San Donato Milanese, Italy

[22] Filed: July 19, 1974

[21] Appl. No.: 489,919

[30] Foreign Application Priority Data
July 20, 1973 Italy.................................. 26816/73

[52] U.S. Cl.................................. 203/58; 203/71; 260/681.5 R; 252/364
[51] Int. Cl.². .................... C07C 7/08; B01D 11/04
[58] Field of Search ......... 252/364; 260/309, 309.7, 260/681.5 R; 203/58

[56] References Cited
UNITED STATES PATENTS

| | | | |
|---|---|---|---|
| 2,437,357 | 3/1948 | McKinnis | 203/58 |
| 2,484,305 | 10/1949 | Mayland et al. | 260/681.5 R |
| 2,589,960 | 11/1947 | Ray | 252/364 |
| 3,784,626 | 1/1974 | Ginnasi et al. | 260/681.5 R |
| 3,819,529 | 6/1974 | Murphy | 252/364 X |
| 3,843,676 | 10/1974 | Spaenig et al. | 260/309 |

OTHER PUBLICATIONS
"Chemical Abstracts", vol. 66 (1967), 10992p.

*Primary Examiner*—Benjamin R. Padgett
*Assistant Examiner*—David Lelance
*Attorney, Agent, or Firm*—Ralph M. Watson

[57] ABSTRACT

A diolefin (isoprene or butadiene) is separated from a mixture thereof with other hydrocarbons by feeding the mixture to an extractive distillation column at a point intermediate its ends and also feeding to that column, at a point adjacent its upper end, an imidazole derivative, such as N-methyl imidazole, which is a solvent for the diolefin, withdrawing substantially all of the other hydrocarbons from the upper end of the column and withdrawing the solvent, substantially all of the diolefin and the balance of the other hydrocarbons as bottom product from that first extractive distillation column. That bottom product is then fed to a second extractive distillation column, the diolefin is withdrawn from its upper end in substantially pure form, the balance of the other hydrocarbons are withdrawn in vapor phase and the solvent is withdrawn from the lower end of the second extractive distillation column for recycle to the first and second extractive distillation columns.

5 Claims, 2 Drawing Figures

SOLVENT SEPARATION OF DIOLEFINS FROM MIXTURES CONTAINING THE SAME

The present invention relates to the solvent separation of diolefins from mixtures containing the same.

More particularly the solvent separation according to the present invention can be used:

a. for the separation of isoprene from mixtures containing besides isoprene other $C_5$ saturated and unsaturated hydrocarbons and in particularly cyclopentadiene.

b. for the separation of butadiene from mixtures of $C_4$ hydrocarbons containing the same.

The solvent in accordance with the present invention can be indifferently used both for the separation of a group of diolefins from a mixture of said diolefins with saturated and olefinic hydrocarbons and for the separation of single diolefins from each other.

Many solvents are known for the aforesaid separations but they generally present the drawbacks hereinbelow described.

In the separation of a diolefin from a mixture containing saturated and olefinic hydrocarbons and other diolefins, many solvents are suitable for the separation of the diolefins from the saturated and olefinic hydrocarbons but not suitable for a satisfactory separation of the diolefins from each other.

Among such solvents there is for instance N-methyl pyrrolidone. Other solvents (for instance aniline) make it possible to carry out in a satisfactory way only the separation of diolefins from each other (see French Pat. No. 2,017,017).

Moreover some solvents show a very high solvent power but a low selectivity; others, on the contrary, such as sulfolane, show a high selectivity but a low solvent power.

It has been found, and this constitutes the subject of the present invention, that heterocyclic compounds having 5 carbon atoms, saturated or unsaturated, with 2 N atoms in the ring (in not vicinal position), with or without one or more oxygen atoms bound to the carbons of the ring, mono-or dialkylated with at least one alkyl group bound to an N atom (the alkyl group can indifferently be a methyl or ethyl group), alone or in admixture, very good solvents by means of which it is possible to overcome the drawbacks of the known art.

Furthermore they present both a very high solvent power and selectivity.

It is to be noted moreover that such solvents do not hydrolize to dimethyl formamide and this constitutes an important advantage since the properties of the solvent remain constant so that it does not need to be replenished in the plant.

In the class of the above defined solvents there are particularly included: N-methyl imidazole, N-N' dimethyl imidazolidin 2 one, 1.2 dimethyl imidazole.

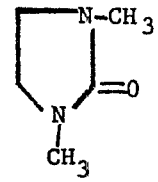

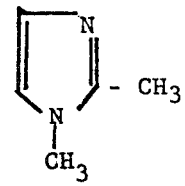

The solvents employed in the practice of the present invention can be used as such or in admixture with each other and advantageously in admixture with up to 20% by weight of water; in any case they do not present corrosion phenomena either when anhydrous or when in admixture with water.

The solvents employed in the practice of our invention can be used as such or in admixture for the separation of the above reported compounds or classes of compounds either in processes wherein extractive distillations are used, or in processes wherein liquid-liquid extractions are used or at processes wherein both extractive distillations and liquid-liquid extractions are used.

Figure 1:
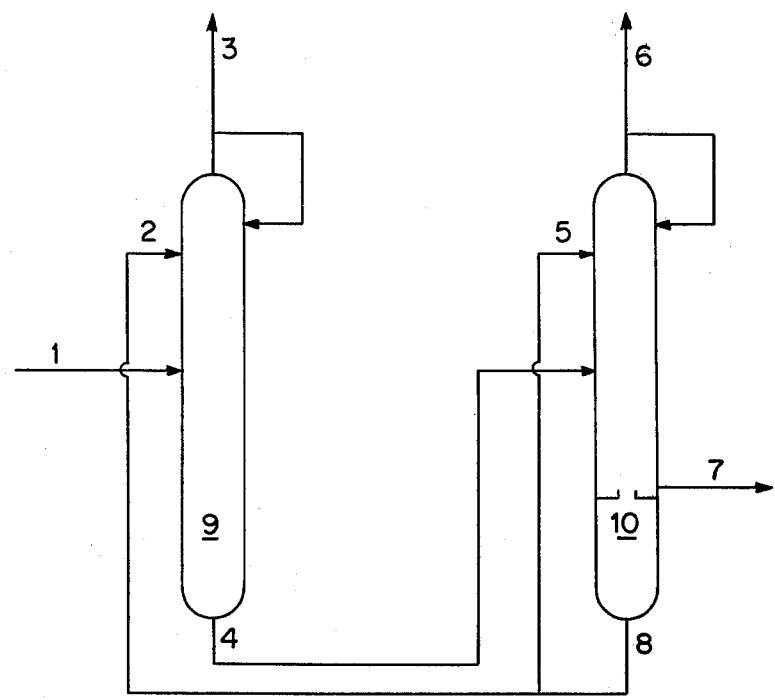
FIG. 1 is a schematic illustration of one form of apparatus adapted for use in the practice of our invention.

Some examples will now be given to illustrate in a better way the invention without restricting the same. In Examples 1 and 2 reference is made to FIG. 1.

EXAMPLE 1

We fed to the extractive distillation column 9 a stream (line 1) of:

| | | |
|---|---|---|
| Isoprene | = | 282.000 moles/hour |
| 1.4 Pentadiene | = | 1.346 moles/hour |
| 2 butene | = | 0.010 moles/hour |
| Isopentane | = | 13.241 moles/hour |
| 1 pentene | = | 39.664 moles/hour |
| 2 methyl 1 butene | = | 67.257 moles/hour |
| Isopropenylacetylene | = | 0.055 moles/hour |
| normal pentane | = | 120.090 moles/hour |
| 2 pentene trans | = | 29.354 moles/hour |
| 2 pentene cis | = | 18.055 moles/hour |
| 2 methyl 2 butene | = | 11.258 moles/hour |
| 1.3 cyclopentadiene | = | 1.682 moles/hour |
| 1.3 pentadiene trans | = | 1.471 moles/hour |
| The working conditions were the following: | | |
| Overhead pressure | = | 1.2 atmospheres |
| L/D | = | 1 |
| Plates | = | 70 |

To the same column, through line 2, we fed 673 kg/hour of solvent constituted by a mixture of N-methyl imidazole-water (ratio 94/6 by weight).

As overhead product through line 3 we discharged a stream constituted by:

| | | |
|---|---|---|
| Isoprene | = | 2.700 moles/hour |
| 1.4 pentadiene | = | 1.346 moles/hour |
| Isopentane | = | 13.241 moles/hour |
| 1 pentene | = | 39.664 moles/hour |
| 2 methyl 1 butene | = | 67.257 moles/hour |
| normal pentane | = | 120.090 moles/hour |
| 2 pentene trans | = | 29.354 moles/hour |
| 2 pentene cis | = | 18.055 moles/hour |
| 2 methyl 2 butene | = | 10.979 moles/hour |

The stream coming from the bottom of column 9 (line 4) was sent to the second extractive distillation column 10 together with a stream (line 5) of about 69 kg/hour of solvent constituted by a mixture of N-methyl imidazole and water in the ratio 94/6 by weight.

The separation in 10 was carried out under the following conditions:

| | | |
|---|---|---|
| Overhead pressure | = | 1.2 atmospheres |
| L/D | = | 1 |
| Plates | = | 80 |

As overhead product we discharged through line 6 a high purity isoprene stream, constituted in particular by:

| | | |
|---|---|---|
| Isoprene | = | 274.000 moles/hour |
| 2 methyl 2 butene | = | 0.279 |
| 1.3 pentadiene trans | = | 0.940 |

From a withdrawal pipe (7) we discharged in vapour phase the acetylene hydrocarbons and the dienic hydrocarbons having high polarity (butene 2, isopropenylacetylene, 1.3 cyclopentadiene), while the solvent, free from hydrocarbons, suitable to be used in the aforesaid extractive distillation columns 9 and 10 was discharged from the bottom (line 8).

EXAMPLE 2

We fed to the extractive distillation column 9 1 kg/hour a stream of constituted by (line 1)

| | |
|---|---|
| $C_4$ saturated hydrocarbons | 20% by weight |
| $C_4$ olefinic hydrocarbons | 45% by weight |
| 1.3 butadiene | 35% by weight |
| acetylenic compounds | 1000% ppm |
| The working conditions were the following: | |
| Overhead pressure = | 4 atmospheres |
| L/D = | 1 |
| Plates = | 70 |

To the same column, through line 2, we fed about 11 kg/hour of solvent constituted by a mixture of N-N' dimethyl imidazolidin 2 one and water at the ratio 93/7 by weight.

From the top through line 3 a stream of 0.65 kg/hour was discharged containing substantially saturated and olefinic hydrocarbons. The stream coming from the bottom of column 9 (line 4) was fed to the second extractive distillation column 10 together with a stream of about 2.5 kg/hour (line 5) of solvent constituted by a mixture of N-N' dimethyl imidazolidin 2 one and water (ratio 93/7 by weight).

The separation in column 10 was carried out under the following conditions:

| | | |
|---|---|---|
| Overhead pressure | = | 4 atmospheres |
| L/D | = | 1 |
| Plates | = | 80 |

From the column top we discharged (line 6) a stream of about 0.345 kg/hour of high purity 1.3 butadiene in particular containing acetylenic compounds in amount lower than or equal to 20 ppm.

From a withdrawal pipe we discharged in vapour phase (line 7) the acetylenic hydrocarbons together with a negligible amount of butadiene (0.005 kg/hour) while from the bottom we discharged the solvent (line 8), free from hydrocarbons, suitable to be used again, in the aforesaid extractive distillation columns 9 and 10.

EXAMPLE 3

Figure 2:
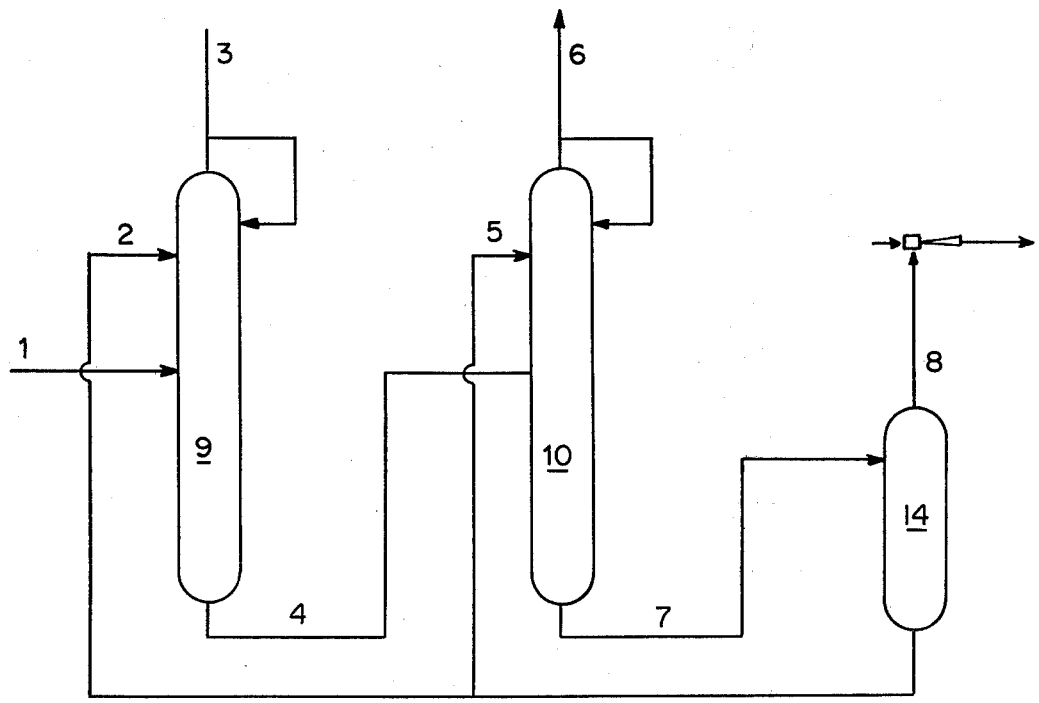
FIG. 2 is a schematic illustration of a modified form of apparatus adapted for use in the practice of our invention.

With reference to the scheme illustrated in FIG. 2 we fed (line 1) to the extractive distillation column (9) a stream equal to the one reported in example 1.

The conditions were the following:

| | | |
|---|---|---|
| Overhead pressure | = | 1.1 atmospheres |
| L/D | = | 1.3 |
| Plates | = | 70 |

To the same column through line 2, we fed about 730 kg/hour of anhydrous 1.2 dimethyl imidazole.

From the top we discharged (line 3) a stream equal to the one reported for the same point in example 1.

The stream leaving the bottom of column 9 (line 4) was fed to the second extractive distillation column 10, together with a stream of about 80 kg/hour (line 5) of anhydrous 1.2 dimethyl imidazole. The separation in column 10 was carried out under the following conditions:

| | | |
|---|---|---|
| Overhead pressure | = | 1.1 atmospheres |
| L/D | = | 1.1 |
| Plates | = | 70 |

From the top we discharged (line 6) a high purity isoprene stream, in particular constituted by:

| | | |
|---|---|---|
| isoprene | = | 268.000 moles/hour |
| 2 methyl 2 butene | = | 0.279 moles/hour |
| 1.3 pentadiene trans | = | 0.840 moles/hour |

From the bottom we discharged a stream (line 7) containing, besides the solvent, all the acetylenic and dienic hydrocarbons (butine 2, isopropenylacetylene, 1.3 cyclopentadiene). This stream was fed to the stripping column (14), working under the following conditions:

| | | |
|---|---|---|
| Overhead pressure | = | 0.8 atmospheres |
| L/D | = | 0 |
| Plates | = | 20 |

From the top we removed (line 8) the aforesaid polar hydrocarbons while from the bottom the solvent suitable to be used again in the aforesaid extractive distillation columns 9 and 10 was discharged.

What we claim is:

1. The method of separating a diolefin from a mixture thereof with other hydrocarbons which comprises, feeding said mixture to a first extractive distillation column at a point intermediate its ends, feeding to said first extractive distillation column at a point adjacent its upper end a solvent for said diolefin selected from the members of the group consisting of the saturated and unsaturated derivatives of imidazole having a methyl or ethyl group bound to at least one nitrogen atom and mixtures thereof with each other and with water, withdrawing substantially all of said other hydrocarbons from the upper end of said column and withdrawing the solvent, substantially all of said diolefin and the balance of the other hydrocarbons as bottom product from said first extractive distillation column, feeding said bottom product to a second extractive distillation column, withdrawing said diolefin from the upper end of the second distillation column in substantially pure form, withdrawing said balance of the other hydrocarbons and said solvent from the second extractive distillation column, and recycling said solvent to said first and second extractive distillation columns.

2. A process as claimed in claim 1 wherein said imidazole derivative is N-methyl imidazole.

3. A process as claimed in claim 1 wherein said imidazole derivative is N-N' dimethyl imidazolin 2 one.

4. A process as claimed in claim 1 wherein said imidazole derivative is 1.2 dimethyl imidazole.

5. A process as claimed in claim 1 wherein said imidazole derivative is used in admixture with water at a percentage of up to 20% by weight.

* * * * *

UNITED STATES PATENT AND TRADEMARK OFFICE
CERTIFICATE OF CORRECTION

PATENT NO. : 3,980,528
DATED : September 14, 1976
INVENTOR(S) : Carlo Rescalli and Alessandro Vetere It is certified that error appears in the above-identified patent and that said Letters Patent are hereby corrected as shown below:

Column 1, line 40, Before "atoms" delete --carbon--.

line 45, Before the comma "," insert --are--.

line 65, To the right of the formula insert

--(N- methyl imidazole)--.

Column 2, line 5, To the right of the formula insert

--(N-N' dimethyl imidozolin 2 one)--.

line 15, To the right of the formula insert

--(1.2 dimethyl imidazole)--.

line 68, Change the dash "-" to --and--.

Column 3, line 46, After "stream" delete --of--.

Signed and Sealed this

Thirty-first Day of May 1977

[SEAL]

Attest:

RUTH C. MASON
*Attesting Officer*

C. MARSHALL DANN
*Commissioner of Patents and Trademarks*